United States Patent [19]
Park et al.

[11] Patent Number: 5,883,038
[45] Date of Patent: *Mar. 16, 1999

[54] SUPPORTED CATALYSTS FOR CONVERTING METHANE OR PURIFIED NATURAL GAS, PREPARATION THEREOF, AND PROCESS FOR PREPARATION OF ETHYLENE USING SAID CATALYSTS

[75] Inventors: Dae Chul Park, Daejon; Pyung Kwon Ahn, Kwangju, both of Rep. of Korea

[73] Assignee: Korea Research Institute of Chemical Technology, Daejon, Rep. of Korea

[*] Notice: The term of this patent shall not extend beyond the expiration date of Pat. No. 5,625,107.

[21] Appl. No.: 549,771
[22] PCT Filed: May 21, 1994
[86] PCT No.: PCT/KR94/00053
  § 371 Date: Nov. 14, 1995
  § 102(e) Date: Nov. 14, 1995
[87] PCT Pub. No.: WO94/27722
  PCT Pub. Date: Dec. 8, 1994

[30] Foreign Application Priority Data

May 22, 1993 [KR] Rep. of Korea ............... 93-8926

[51] Int. Cl.⁶ ............... B01J 23/40; B01J 23/42; B01J 23/44; B01J 23/46
[52] U.S. Cl. ............... 502/325; 502/332; 502/338; 502/339
[58] Field of Search ............... 502/325, 332, 502/338, 339

[56] References Cited

U.S. PATENT DOCUMENTS 3,981,825 9/1976 Reagan et al. ............... 252/455 R
5,077,446 12/1991 Kolts et al. .
5,105,053 4/1992 Jacobson et al. .

*Primary Examiner*—Michael Lewis
*Assistant Examiner*—Alexander G. Ghyka
*Attorney, Agent, or Firm*—Jacobson, Price, Holman & Stern, PLLC

[57] ABSTRACT

Supported catalysts of the following formula (I) for preparing ethylene by conversion of methane or purified natural gas and preparation thereof, and process for preparation of ethylene by direct conversion of methane or purified natural gas using said catalysts:

$$M a'/S \qquad \text{formula (I)}$$

(wherein, M is a compound selected from the group of $RuCl_2(PPh_3)_3$, $RuCl_2(CO)_2(PPh_3)_2$, $Ru_3(CO)_{12}$, $RhCl(CO)(PPh_3)_2$, $IrCl(CO)(PPh_3)_2$, $Pd(PPh_3)_4$, $Pt(PPh_3)_4$, $RuCl_3 \cdot xH_2O$, $RhCl_3 \cdot xH_2O$, $IrCl_3 \cdot xH_2O$, $PdCl_2 \cdot xH_2O$, $H_2PtCl_6 \cdot xH_2O$, S is an inorganic carrier selected from $\alpha\text{-}Al_2O_3$, $\gamma\text{-}Al_2O_3$, $SiO_2$, $SiO_2\text{—}Al_2O_3$, Y-zeolite, MgO and $TiO_2$, a' is weight percentage of metal in catalyst, ranging from 0.25 to 5 wt %.)

21 Claims, No Drawings

SUPPORTED CATALYSTS FOR CONVERTING METHANE OR PURIFIED NATURAL GAS, PREPARATION THEREOF, AND PROCESS FOR PREPARATION OF ETHYLENE USING SAID CATALYSTS

FIELD OF THE INVENTION

The present invention relates to supported catalysts of the following formular (I) for producing ethylene which is used in basic reactions including polymerization, copolymerization and polycondensation reaction in the field of petrochemical industry and fine chemical industry, and preparation thereof.

$$Ma'/S \quad \text{formula (I)}$$

Further, the present invention is to provide a new process for preparation of ethylene by converting directly methane or purified natural gas, in the presence of the above catalyst with nitrogen, at a temperature of about 670° to 850° C., preferably in the range of 710° to 810° C., which is distinctly lower reaction temperature relative to that of conventional synthesis of hydrocarbon(s) by dehydrogenation. By this process, ethylene is obtained in short time, with high yield, and without by-product such as CO, $CO_2$, contrary to oxidative coupling reaction where oxygen is introduced.

In Ma'/S of above mentioned general formular (I), M is a compound selected from the group of $RuCl_2(PPh_3)_3$, $RuCl_2(CO)_2(PPh_3)_2$, $Ru_3(CO)_{12}$, $RhCl(CO)(PPh_3)_2$, $IrCl(CO)(PPh_3)_2$, $Pd(PPh_3)_4$, $Pt(PPh_3)_4$, $RuCl_3 \cdot xH_2O$, $RhCl_3 \cdot xH_2O$, $IrCl_3 \cdot xH_2O$, $PdCl_2 \cdot xH_2O$, wherein x is 3–10, $H_2PtCl_6 \cdot xH_2O$, S is an inorganic carrier selected from $\alpha$-$Al_2O_3$, $\gamma$-$Al_2O_3$, $SiO_2$, $SiO_2$—$Al_2O_3$, Y-zeolite, MgO and $TiO_2$, a' is weight percentage of metal in catalyst, ranging from 0.25 to 5 wt %.

BACKGROUND ART

Few of literatures and patents about the catalyst which can be used to produce ethylene by direct conversion of methane is disclosed; moreover, it is different in technical field from present invention. By conventional processes, large amounts of by-product such as carbon dioxide are produced, separation and removal thereof is difficult and environmental pollution is likely to be caused. Also, synthesis of hydrocarbon(s) by conventional dehydrogenation is conducted at relatively high temperature of about 1500° to 1550° C. through thermal or electric cracking reaction to cause some problems such as necessity of supply of high energy, expense of high temperature equipment (plan) as well as enormous loss of thermal energy expense, particulary severe corrosion of reactor.

As prior art describing synthesis of hydrocarbon by oxidative coupling or dehydrogenation reaction, there are U.S. Pat. Nos. 5,066,629, 5,068,486 and 5,118,654, Canadian patent no. 2016675 and Japanese patent nos. 04352730, 04368342.

SUMMARY OF THE INVENTION

Until now, new catalyst being able to conduct conversion reaction not at so (ultra) high temperature as that of process for synthesis of hydrocarbons by dehydrogenation but at distinctly lower (mid•low) temperature, and new process for producing said catalyst, and new process for conversion into ethylene using said catalyst have always been expected.

To meet the expectations above, as the result of study for years, the inventors completed development of a new catalyst, preparation thereof, and a simple process for obtaining ethylene in short time, with high yield and with trace amounts of impurities, by converting methane or purified natural gas in the presence of said catalyst at distinctly lower temperature compared to that of process for synthesis of hydrocarbon by dehydrogenation or oxidative coupling reaction; thus direct conversion of methane, being carried out at distinctly low temperature, causes to save enormous amount of thermal energy cost that was needed in synthesis reaction of hydrocarbon(s) by dehydrogenation or oxidative coupling reaction, and is sufficiently efficient to environmental pollution problems through reduced amounts of impurities, namely $CO_2$.

DETAILED DESCRIPTION OF THE INVENTION

The present invention will be described in further detail with reference to Examples.

First, new desirable catalyst is produced by supporting organic transition metal compound on inorganic carriers, i.e., by supporting various metal cluster compound and organic metal complex on inorganic carriers.

In this method, process for synthesis and purification of catalyst is much easier than that in other processes.

Through development of this catalyst, reaction conditions such as reaction temperature, reaction pressure are mitigated considerably and ethylene is produced with high yield.

Further, due to development of process using catalyst of the present invention, the process for preparation of ethylene is simplified, as a result, productivity is enhanced.

The present invention is described in detail as follows.

In the present invention, by developing a new process where methane or purified natural gas is converted directly to ethylene, which is different from synthesis reaction of hydrocarbon by dehydrogenation or oxidative coupling reaction, overall process is simplified, further, reaction temperature is lowered to a temperature of about 670° to 850° C., preferably in the range of 710° to 810° C., and amounts of impurities such as carbon dioxide are greatly reduced.

In the present invention, by using $RuCl_2(PPh_3)_3$, $RuCl_2(CO)_2(PPh_3)_2$, $RhCl(CO)(PPh_3)_2$ catalyst, ethylene is produced with high yield at a temperature of about 810° C. At this time, conversion rate is maintained in the range of about 7.5 to 8.3% and through continuous recirculation of raw material introduced, conversion rate is maximized.

That is to say, through solid surface reaction using heterogeneous catalyst, reaction conditions such as reaction temerature and pressure are considerably mitigated, at the same time, reaction equipment is simplified.

Process for preparing supported catalyst of the present invention is as follows.

Metal cluster (compound) and organic metal complex are dissolved in mixed solvent such as dichloromethane and acetone, etc.

Then, inorganic carrier is added to this solution, and metal cluster (compound) and organic metal complex are immersed into inorganic carrier by stirring at about 20° to 200° C., then dried in vacuum drier to prepare catalyst.

Inorganic carriers used here are $\alpha$-$Al_2O_3$, $\gamma$-$Al_2O_3$, $SiO_2$, $SiO_2$—$Al_2O_3$, Y-zeolite, MgO and $TiO_2$.

And metal cluster(compound) and organic metal complex compounds used are $RuCl_2(PPh_3)_3$, $RuCl_2(CO)_2(PPh_3)_2$, $Ru_3(CO)_{12}$, $RhCl(CO)(PPh_3)_2$, $IrCl(CO)(PPh_3)_2$, $Pd(PPh_3)_4$, $Pt(PPh_3)_4$, $RuCl_3 \cdot xH_2O$, $RhCl_3 \cdot xH_2O$, $IrCl_3 \cdot xH_2O$, $PdCl_2 \cdot xH_2O$, $H_2PtCl_6 \cdot xH_2O$.

According to the experiments of the present invention, the optimum inorganic carriers for preparation of ethylene are $\alpha\text{-Al}_2\text{O}_3$ and MgO, and metal of VIII series are Ru, Rh.

Reaction conditions in the presence of new catalyst of the present invention are as follows.

Dilution ratio of nitrogen to methane or purified natural gas is 1 to 6, preferably 1 to 3, based on methane.

Reaction temperature is about 670° to 850° C., preferably in the range of 710° to 810° C.

Concentration of catalyst is below 5 wt %, prefarably 1 to 3 wt %.

Space velocity of source gas is about 75 to 1200 $hr^{-1}$, prefarably in the range of 150 to 600 $hr^{-1}$.

Reaction pressure is usually about 1 to 5 atm, preferably normal pressure.

Conversion rate of methane or purified natural gas, and yield and selectivity of ethylene are defined as follows.

$$\text{conversion rate (mol \%)} = \frac{\text{mol numbers of methane reacted}}{\text{mol numbers of methane supplied}} \times 100$$

$$\text{yield (mol \%)} = \frac{\text{mol numbers of } C_2 \text{ hydrocarbon such as ethylene produced}}{\text{mol numbers of methane supplied}} \times 100$$

$$\text{selectivity (mol \%)} = \frac{\text{mol numbers of } C_2 \text{ hydrocarbon such as ethylene produced}}{\text{mol numbers of methane reacted}} \times 100$$

or $$\text{conversion rate (mol \%)} = \frac{\text{mol numbers of methane in purified natural gas reacted}}{\text{mol numbers of methane in purified natural gas supplied}} \times 100$$

$$\text{yield (mol \%)} = \frac{\text{mol numbers of } C_2 \text{ hydrocarbon compound such as ethylene produced}}{\text{mol numbers of methane in purified natural gas supplied}} \times 100$$

$$\text{selectivity (mol \%)} = \frac{\text{mol numbers of } C_2 \text{ hydrocarbon compound such as ethylene produced}}{\text{mol numbers of methane in purified natural gas reacted}} \times 100$$

Reactants and products are analyzed by gas chromatograph.

Examples 1 to 8 relate to new catalyst and process for preparation thereof, Exmaples 9 to 31 relate to new process for producing ethylene by conversion reaction of methane or purified natural gas in the presence of new catalyst of the present invention.

EXAMPLE 1

$\alpha\text{-Al}_2\text{O}_3$ 4.39 g, $\text{RuCl}_2(\text{PPh}_3)_3$ 0.85 g (0.886 mmol) are added to mixed solvent consisting of 20 ml of dichloromethane and 10 ml of acetone. This suspension is stirred for about 30 minutes at a temperature of around 40° C., and evaporated to dryness by distillation under reduced pressure, then dried in vacuum drier for about 20 hours to prepare $\text{RuCl}_2(\text{PPh}_3)_3/\alpha\text{-Al}_2\text{O}_3$ catalyst.

EXAMPLE 2

$\text{RuCl}_2(\text{CO})_2(\text{PPh}_3)_2$ 0.56 g (0.744 mmol) is added to mixed solvent consisting of 40 ml of dichloromethane and 10 ml of acetone and dissolved, then $\alpha\text{-Al}_2\text{O}_3$ 3.68 g is added thereto. This suspension is stirred for about 30 minutes at a temperature of around 40° C. and solvent is evaporated by distillation under reduced pressure. Then residue obtained is dried in vacuum drier for about 20 hours to prepare $\text{RuCl}_2(\text{CO})_2(\text{PPh}_3)_2/\alpha\text{-Al}_2\text{O}_3$ catalyst.

EXAMPLE 3

$\alpha\text{-Al}_2\text{O}_3$ 3.95 g, $\text{Ru}_3(\text{CO})_{12}$ 0.17 g (0.266 mmol) are added to mixed solvent consisting of 10 ml of dichloromethane and 100 ml of acetone and dissolved.

This suspension is stirred for about 30 minutes at a temperature of around 40° C. and solvent is evaporated by distillation under reduced pressure.

Residue obtained is dried in vacuum drier for about 20 hours to prepare $\text{Ru}_3(\text{CO})_{12}/\alpha\text{-Al}_2\text{O}_3$ catalyst.

EXAMPLE 4

$\alpha\text{-Al}_2\text{O}_3$ 3.28 g, $\text{RhCl}(\text{CO})(\text{PPh}_3)_2$ 0.45 g (0.652 mmol) are added to mixted solvent consisting of 40 ml of dichloromethane and 20 ml of acetone and dissolved.

This suspension is stirred for about 30 minutes at a temperature of around 40° C. and solvent is evaporated by distillation under reduced pressure.

Residue obtained is dried in vacuum drier for about 20 hours to prepare $\text{RhCl}(\text{CO})(\text{PPh}_3)_2/\alpha\text{-Al}_2\text{O}_3$ catalyst.

EXAMPLE 5

$\alpha\text{-Al}_2\text{O}_3$ 3.14 g, $\text{IrCl}(\text{CO})(\text{PPh}_3)_2$ 0.26 g (0.333 mmol) are added to mixed solvent consisting of 60 ml of dichloromethane and 10 ml of acetone and dissolved.

This suspension is stirred for about 30 minutes at a temperature of around 40° C. and solvent is evaporated by distillation under reduced pressure.

Residue obtained is dried in vacuum drier for about 20 hours to prepare $\text{IrCl}(\text{CO})(\text{PPh}_3)_2/\alpha\text{-Al}_2\text{O}_3$ catalyst.

EXAMPLE 6

$\alpha\text{-Al}_2\text{O}_3$ 3.79 g, $\text{Pd}(\text{PPh}_3)_4$ 0.84 g (0.727 mmol) are added to mixted solvent consisting of 20 ml of dichloromethane and 10 ml of acetone and dissolved.

This suspension is stirred for about 30 minutes at a temperature of around 40° C. and solvent is evaporated by distillation under reduced pressure.

Residue obtained is dried in vacuum drier for about 20 hours to prepare $\text{Pd}(\text{PPh}_3)_4/\alpha\text{-Al}_2\text{O}_3$ catalyst.

EXAMPLE 7

$\alpha\text{-Al}_2\text{O}_3$ 4.45 g, $\text{Pt}(\text{PPh}_3)_4$ 0.58 g (0.466 mmol) are added to mixted solvent consisting of 20 ml of dichloromethane and 10 ml of acetone and dissolved.

This suspension is stirred for about 30 minutes at a temperature of around 40° C. and solvent is evaporated by distillation under reduced pressure.

Residue obtained is dried in vacuum drier for about 20 hours to prepare $\text{Pt}(\text{PPh}_3)_4/\alpha\text{-Al}_2\text{O}_3$ catalyst.

EXAMPLE 8

$\gamma\text{-Al}_2\text{O}_3$ 4.39g, $\text{RuCl}_2(\text{PPh}_3)_3$ 0.85 g (0.886 mmol) are added to mixed solvent consisting of 20 ml of dichloromethane and 10 ml of acetone and stirred for about 30 minutes at a temperature of around 40° C. This suspension is evaporated to dryness by distillation under reduced pressure, then dried in vacuum drier for about 20 hours to prepare $\text{RuCl}_2(\text{PPh}_3)_3/\gamma\text{-Al}_2\text{O}_3$ catalyst.

EXAMPLE 9

Except using $SiO_2$ 4.39 g as inorganic carrier, Example 8 is repeated to prepare $RuCl_2(PPh_3)_3/SiO_2$ catalyst.

EXAMPLE 10

Except using $SiO_2$—$Al_2O_3$ 4.39 g as inorganic carrier, Example 8 is repeated to prepare $RuCl_2(PPh_3)_3/SiO_2$—$Al_2O_3$ catalyst.

EXAMPLE 11

Except using Y-zeolite 4.39 g as inorganic carrier, Example 8 is repeated to prepare $RuCl_2(PPh_3)_3$/Y-zeolite catalyst.

EXAMPLE 12

Except using MgO 4.39 g as inorganic carrier, Example 8 is repeated to prepare $RuCl_2(PPh_3)_3/MgO$ catalyst.

EXAMPLE 13

Except using $TiO_2$ 4.39 g as inorganic carrier, Example 8 is repeated to prepare $RuCl_2(PPh_3)_3/TiO_2$ catalyst.

EXAMPLE 14

$\alpha$-$Al_2O_3$ 5.01 g, $RuCl_3 \cdot xH_2O$ 0.21 g (1.012 mmol) are added to mixed solvent consisting of 20 ml of dichloromethane and 10 ml of acetone and stirred for about 30 minutes at a temperature of around 40° C.

This suspension is evaporated to dryness by distillation under reduced pressure, then dried in vacuum drier for about 20 hours to prepare $RuCl_3 \cdot xH_2O/\alpha$-$Al_2O_3$ catalyst.

EXAMPLE 15

Except that $\alpha$-$Al_2O_3$ 3.62 g, $RhCl_3 \cdot xH_2O$ 0.15 g (0.717 mmol) are added to mixed solvent consisting of 10 ml of dichloromethane and 20 ml of ethanol, Example 14 is repeated to prepare $RhCl_3 \cdot xH_2O/\alpha$-$Al_2O_3$ catalyst.

EXAMPLE 16

Except $\alpha$-$Al_2O_3$ 3.79 g, $IrCl_3 \cdot xH_2O$ 0.12 g (0.402 mmol) are added to 20 ml of N,N-Dimethylformamide, and stirred at a temperature of around 150° C., Example 14 is repeated to prepare $IrCl_3 \cdot xH_2O/\alpha$-$Al_2O_3$ catalyst.

EXAMPLE 17

$\alpha$-$Al_2O_3$ 3.53 g, $PdCl_2 \cdot xH_2O$ 0.12 g (0.677 mmol) are dissolved in mixed aqueous sollution of distilled water 30 ml and 35% conc. HCl 1 ml, then stirred for about 30 minutes at around 100° C.

This suspension is evaporated to dryness by distillation under reduced pressure, then dried in vacuum drier for about 20 hours to prepare $PdCl_2 \cdot xH_2O/\alpha$-$Al_2O_3$ catalyst.

EXAMPLE 18

Except using $H_2PtCl_6 \cdot xH_2O$ 0.15 g (0.366 mmol), Example 14 is repeated to prepare $H_2PtCl_6 \cdot xH_2O/\alpha$-$Al_2O_3$ catalyst.

EXAMPLE 19

Methane (or purified natural gas) and nitrogen are introduced each at the flow rate of about 10 ml/min into continuous stationary phase flow reactor (inner diameter: 0.70 cm; length: 40 cm; stuff: stainless steel 316) in the presence of the catalyst prepared in Example 1. Products are obtained by continuous reaction under about 1 atm at each reaction temperature which is given in following Table 1 and the results of analysis of them by gas chromatography is as following Table 1 (from this example to Example 31, raw material is continuously reintroduced to convesion reaction).

Below mentioned * mark represents reaction is conducted at surrounding temperature based on given value.

TABLE 1

| Reaction Temp. | Conversion | Yield (%) | | Selectivity (%) | |
|---|---|---|---|---|---|
| *(°C.) | (%) | Ethylene | Ethane | Ethylene | Ethane |
| 710 | about 2.0 | about 1.1 | about 0.9 | about 55.0 | about 45.0 |
| 730 | about 2.9 | about 2.1 | about 0.8 | about 72.4 | about 27.6 |
| 750 | about 4.4 | about 3.6 | about 0.8 | about 81.8 | about 18.2 |
| 770 | about 5.4 | about 4.8 | about 0.6 | about 88.9 | about 11.1 |
| 790 | about 6.6 | about 6.0 | about 0.6 | about 90.9 | about 9.1 |
| 810 | about 7.5 | about 6.8 | about 0.7 | about 90.7 | about 9.3 |

EXAMPLE 20

Except using $RuCl_2(CO)_2(PPh_3)_2/\alpha$-$Al_2O_3$ as catalyst, Example 19 is repeated and the distribution of resultant products is as following Table 2.

TABLE 2

| Reaction Temp. | Conversion | Yield (%) | | Selectivity (%) | |
|---|---|---|---|---|---|
| *(°C.) | (%) | Ethylene | Ethane | Ethylene | Ethane |
| 710 | about 2.1 | about 1.2 | about 0.9 | about 57.1 | about 42.9 |
| 730 | about 3.1 | about 2.1 | about 1.0 | about 67.7 | about 32.3 |
| 750 | about 4.5 | about 3.7 | about 0.8 | about 82.2 | about 17.8 |
| 770 | about 5.6 | about 4.9 | about 0.7 | about 87.5 | about 12.5 |
| 790 | about 6.5 | about 5.9 | about 0.6 | about 90.8 | about 9.2 |
| 810 | about 7.9 | about 7.3 | about 0.6 | about 92.4 | about 7.6 |

EXAMPLE 21

Except using $Ru_3(CO)_{12}/\alpha$-$Al_2O_3$ as catalyst, Example 19 is repeated and the distribution of resultant products is as following Table 3.

TABLE 3

| Reaction Temp. | Conversion | Yield (%) | | Selectivity (%) | |
|---|---|---|---|---|---|
| *(°C.) | (%) | Ethylene | Ethane | Ethylene | Ethane |
| 710 | about 1.4 | about 0.5 | about 0.9 | about 35.7 | about 64.3 |
| 730 | about 2.6 | about 1.6 | about 1.0 | about 61.5 | about 38.5 |
| 750 | about 3.8 | about 2.8 | about 1.0 | about 73.7 | about 26.3 |
| 770 | about 4.6 | about 3.7 | about 0.9 | about 80.4 | about 19.6 |
| 790 | about 6.4 | about 5.1 | about 1.3 | about 79.7 | about 20.3 |
| 810 | about 7.3 | about 5.9 | about 1.4 | about 80.8 | about 19.2 |

EXAMPLE 22

Except using $RhCl(CO)(PPh_3)_2/\alpha$-$Al_2O_3$ as catalyst, Example 19 is repeated and the distribution of resultant products is as following Table 4.

TABLE 4

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 2.2 | about 1.2 | about 1.0 | about 54.5 | about 45.5 |
| 730 | about 2.6 | about 1.8 | about 0.8 | about 69.2 | about 30.8 |
| 750 | about 4.4 | about 3.4 | about 1.0 | about 77.3 | about 22.7 |
| 770 | about 5.5 | about 4.7 | about 0.8 | about 85.5 | about 14.5 |
| 790 | about 6.7 | about 6.0 | about 0.7 | about 89.6 | about 10.4 |
| 810 | about 8.3 | about 7.6 | about 0.7 | about 91.6 | about 8.4 |

EXAMPLE 23

Except using $IrCl(CO)(PPh_3)_2/\alpha-Al_2O_3$ as catalyst, Example 19 is repeated and the distribution of resultant products is as following Table 5.

TABLE 5

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 1.3 | about 0.6 | about 0.7 | about 46.2 | about 53.8 |
| 730 | about 2.5 | about 1.8 | about 0.7 | about 72.0 | about 28.0 |
| 750 | about 3.6 | about 2.6 | about 1.0 | about 72.2 | about 27.8 |
| 770 | about 5.1 | about 4.3 | about 0.8 | about 84.3 | about 15.7 |
| 790 | about 6.1 | about 5.4 | about 0.7 | about 88.5 | about 11.5 |
| 810 | about 7.3 | about 6.7 | about 0.6 | about 91.8 | about 8.2 |

EXAMPLE 24

Except using $Pd(PPh_3)_4/\alpha-Al_2O_3$ as catalyst, Example 19 is repeated and the distribution of resultant products is as following Table 6.

TABLE 6

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 1.1 | about 0.5 | about 0.6 | about 45.5 | about 54.5 |
| 730 | about 1.5 | about 0.9 | about 0.6 | about 60.0 | about 40.0 |
| 750 | about 3.6 | about 2.6 | about 1.0 | about 72.2 | about 27.8 |
| 770 | about 5.2 | about 4.1 | about 1.1 | about 78.8 | about 21.2 |
| 790 | about 5.9 | about 5.1 | about 0.8 | about 86.4 | about 13.6 |
| 810 | about 7.2 | about 6.7 | about 0.6 | about 93.1 | about 6.9 |

EXAMPLE 25

Except using $Pt(PPh_3)_4/\alpha-Al_2O_3$ as catalyst, Example 19 is repeated and the distribution of resultant products is as following Table 7.

TABLE 7

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 1.2 | about 0.6 | about 0.6 | about 50.0 | about 50.0 |
| 730 | about 1.8 | about 1.1 | about 0.7 | about 61.1 | about 38.9 |
| 750 | about 3.0 | about 2.3 | about 0.7 | about 76.7 | about 23.3 |
| 770 | about 4.6 | about 3.8 | about 0.8 | about 82.6 | about 17.4 |
| 790 | about 5.8 | about 5.1 | about 0.7 | about 87.9 | about 12.1 |
| 810 | about 7.3 | about 6.6 | about 0.7 | about 90.4 | about 9.6 |

EXAMPLE 26

Except using $RuCl_2(PPh_3)_3/\gamma-Al_2O_3$ as catalyst, Example 19 is repeated and the distribution of resultant products is as following Table 8.

TABLE 8

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 1.4 | about 1.0 | about 0.4 | about 71.4 | about 28.6 |
| 730 | about 1.8 | about 1.3 | about 0.5 | about 72.2 | about 27.8 |
| 750 | about 2.3 | about 1.7 | about 0.6 | about 73.9 | about 26.1 |
| 770 | about 2.8 | about 2.1 | about 0.7 | about 75.0 | about 25.0 |
| 790 | about 4.7 | about 3.9 | about 0.8 | about 83.0 | about 17.0 |

EXAMPLE 27

Except using $RuCl_2(PPh_3)_3/SiO_2-Al_2O_3$ as catalyst, Example 19 is repeated and the distribution of resultant products is as following Table 9.

TABLE 9

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 1.3 | about 1.3 | about 0.0 | about 100.0 | about 0.0 |
| 730 | about 1.8 | about 1.2 | about 0.6 | about 66.7 | about 33.3 |
| 750 | about 3.2 | about 2.2 | about 1.0 | about 68.8 | about 31.2 |
| 770 | about 4.1 | about 3.1 | about 1.0 | about 75.6 | about 24.4 |
| 790 | about 5.7 | about 4.9 | about 0.8 | about 86.0 | about 14.0 |

EXAMPLE 28

Except using $RuCl_2(PPh_3)_3/Y$-zeolite as catalyst, Example 19 is repeated and the distribution of resultant products is as following Table 10.

TABLE 10

| Temp. Reaction *(°C.) | Conversion (%) | Yield (%) Ethylene | Yield (%) Ethane | Selectivity (%) Ethylene | Selectivity (%) Ethane |
|---|---|---|---|---|---|
| 710 | about 1.9 | about 1.4 | about 0.5 | about 73.7 | about 26.3 |
| 730 | about 2.6 | about 1.9 | about 0.7 | about 73.1 | about 26.9 |
| 750 | about 4.0 | about 3.0 | about 1.0 | about 75.0 | about 25.0 |
| 770 | about 4.3 | about 3.5 | about 0.8 | about 81.4 | about 18.6 |
| 790 | about 4.8 | about 4.0 | about 0.8 | about 83.3 | about 16.7 |

EXAMPLE 29

Except using $RuCl_2(PPh_3)_3/MgO$ as catalyst, Example 19 is repeated and the distribution of resultant products is as following Table 11.

TABLE 11

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 2.4 | about 1.3 | about 1.1 | about 54.2 | about 45.8 |
| 730 | about 3.2 | about 2.0 | about 1.2 | about 62.5 | about 37.5 |
| 750 | about 4.1 | about 3.1 | about 1.0 | about 75.6 | about 24.4 |
| 770 | about 4.5 | about 3.6 | about 0.9 | about 80.0 | about 20.0 |
| 790 | about 5.9 | about 5.1 | about 0.8 | about 86.4 | about 13.6 |

EXAMPLE 30

Except using $RuCl_3 \cdot xH_2O/\alpha\text{-}Al_2O_3$ as catalyst, Example 19 is repeated and the distribution of resultant products is as following Table 12.

TABLE 12

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 0.0 | about 0.0 | about 0.0 | about 0.0 | about 0.0 |
| 730 | about 0.3 | about 0.0 | about 0.3 | about 0.0 | about 100.0 |
| 750 | about 1.0 | about 0.2 | about 0.8 | about 20.0 | about 80.0 |
| 770 | about 1.8 | about 0.8 | about 1.0 | about 44.4 | about 55.6 |
| 790 | about 2.7 | about 1.7 | about 1.0 | about 63.0 | about 37.0 |

EXAMPLE 31

Except using $RhCl_3 \cdot xH_2O/\alpha\text{-}Al_2O_3$ as catalyst, Example 19 is repeated and the distribution of resultant products is as following Table 13.

TABLE 13

| Reaction Temp. *(°C.) | Conversion (%) | Yield (%) Ethylene | Yield (%) Ethane | Selectivity (%) Ethylene | Selectivity (%) Ethane |
|---|---|---|---|---|---|
| 710 | about 0.0 | about 0.0 | about 0.0 | about 0.0 | about 0.0 |
| 730 | about 0.0 | about 0.0 | about 0.0 | about 0.0 | about 0.0 |
| 750 | about 0.4 | about 0.0 | about 0.4 | about 0.0 | about 100.0 |
| 770 | about 1.7 | about 0.9 | about 0.8 | about 52.9 | about 47.1 |
| 790 | about 3.3 | about 2.4 | about 0.9 | about 72.7 | about 27.3 |

What is claimed is:

1. A catalyst for preparing ethylene by conversion of methane or purified natural gas; said catalyst having the general formula $$Ma'/S \quad (I)$$

wherein, M is a compound selected from the group consisting of $RuCl_2(PPh_3)_3$, $RuCl_2(CO)_2(PPh_3)_2$, $Ru_3(CO)_{12}$, $RhCl(CO)(PPh_3)_2$, $IrCl(CO)(PPh_3)_2$, $Pd(PPh_3)_4$, $Pt(PPh_3)_4$, $RuCl_3 \cdot xH_2O$, $RhCl_3 \cdot xH_2O$, and $PdCl_2 \cdot xH_2C$, x being from 3–10; S is an inorganic carrier selected from the group consisting of $\alpha\text{-}Al_2O_3$, $\gamma\text{-}Al_2O_3$, $SiO_2$, $SiO_2\text{—}Al_2O_3$, Y-zeolite, MgO and $TiO_2$; and a' is an amount of metal corresponding to 0.25 to 5 wt % of the catalyst; wherein M is supported on the inorganic carrier, S.

2. The catalyst of claim 1 wherein M is $RuCl_2(PPh_3)_3$ and S is $\alpha\text{-}Al_2O_3$.

3. The catalyst of claim 1 wherein M is $RuCl_2(CO)_2(PPh_3)_2$ and S is $\alpha\text{-}Al_2O_3$.

4. The catalyst of claim 1 wherein M is $Ru_3(CO)_{12}$ and S is $\alpha\text{-}Al_2O_3$.

5. The catalyst of claim 1 wherein M is $RhCl(CO)(PPh_3)_2$ and S is $\alpha\text{-}Al_2O_3$.

6. The catalyst of claim 1 wherein M is $IrCl(CO)(PPh_3)_2$ and S is $\alpha\text{-}Al_2O_3$.

7. The catalyst of claim 1 wherein M is $Pd(PPh_3)_4$ and S is $\alpha\text{-}Al_2O_3$.

8. The catalyst of claim 1 wherein M is $Pt(PPh_3)_4$ and S is $\alpha\text{-}Al_2O_3$.

9. The catalyst of claim 1 wherein M is $RuCl_2(PPh_3)_3$ and S is $\gamma\text{-}Al_2O_3$.

10. The catalyst of claim 1 wherein M is $RuCl_2(PPh_3)_3$ and S is $SiO_2$.

11. The catalyst of claim 1 wherein M is $RuCl_2(PPh_3)_3$ and S is $SiO_2\text{—}Al_2O_3$.

12. The catalyst of claim 1 wherein M is $RuCl_2(PPh_3)_3$ and S is Y-zeolite.

13. The catalyst of claim 1 wherein M is $RuCl_2(PPh_3)_3$ and S is MgO.

14. The catalyst of claim 1 wherein M is $RuCl_2(PPh_3)_3$ and S is $TiO_2$.

15. The catalyst of claim 1 wherein M is $RuCl_3 \cdot xH_2O$ and S is $\alpha\text{-}Al_2O_3$.

16. The catalyst of claim 1 wherein M is $RhCl_3 \cdot xH_2O$ and S is $\alpha\text{-}Al_2O_3$.

17. The catalyst of claim 1 wherein M is $PdCl_2 \cdot xH_2O$ and S is $\alpha\text{-}Al_2O_3$.

18. The catalyst of claim 1 wherein, in the presence of said catalyst, ethylene is prepared by reacting methane or purified natural gas and nitrogen at a temperature of about 670° C. to 850° C., under a pressure of under 1 to 5 atm.

19. The catalyst of claim 18 wherein the concentration of the catalyst is between 1 to 3 wt %.

20. A process for preparing the catalyst according to claim 1, which comprises the steps of: (a) adding M and S to a single or mixed solvent of dichloromethane and acetone to obtain a suspension; (b) reflux-stirring the suspension at a temperature of about 30° to 250° C.; (c) then, evaporating the solvent by distillation under reduced pressure; and (d) vacuum drying the residue.

21. The process according to claim 20, wherein the suspension is reflux-stirred at a temperature of 40° to 150° C.

* * * * *